United States Patent [19]
Torii et al.

[11] Patent Number: 4,466,880
[45] Date of Patent: Aug. 21, 1984

[54] OXYGEN SENSOR

[75] Inventors: Hideo Torii, Higashiosaka; Hideyuki Okinaka, Settsu; Toshio Ozawa, Hirakata, all of Japan

[73] Assignee: Matsushita Electric Industrial Co., Ltd., Osaka, Japan

[21] Appl. No.: 419,497

[22] Filed: Sep. 17, 1982

[30] Foreign Application Priority Data

Sep. 17, 1981 [JP] Japan .................................. 56-147621

[51] Int. Cl.³ ............................................ G01N 27/46
[52] U.S. Cl. .................................... 204/428; 204/429; 204/1 T
[58] Field of Search .......................... 204/1 S, 428, 429

[56] References Cited

U.S. PATENT DOCUMENTS

| 4,057,477 | 11/1977 | Weyl et al. | 204/428 |
| 4,132,615 | 1/1979 | Linder et al. | 204/428 |
| 4,140,611 | 2/1979 | Yaegashi et al. | 204/428 |
| 4,240,890 | 12/1980 | Watanabe et al. | 204/428 |
| 4,356,065 | 10/1982 | Dietz | 204/429 |

Primary Examiner—R. L. Andrews
Assistant Examiner—Terryence Chapman
Attorney, Agent, or Firm—Wenderoth, Lind & Ponack

[57] ABSTRACT

An oxygen sensor whose sensing element is covered by a cylindrical porous filter cap, prepared by sintering metallic wool such as nickel-chromium alloy wool for protecting the sensing element from damage by mechanical shock and thermal shock due to a high flow pressure of a high temperature gas and for easy determination of sensing response time.

5 Claims, 6 Drawing Figures

યુ4,466,880

OXYGEN SENSOR

BACKGROUND OF THE INVENTION

1. Field of the Invention

This invention relates to an oxygen sensor used for example, for emission control of an automobile engine.

2. Description of the Prior Art

A usual oxygen sensor of the solid electrolyte type which is used for sensing oxygen gas concentration in an exhaust gas is shown in FIG. 1. The sensor has an oxygen ion conductive solid electrolyte element body 1 (sensing body), formed for example of ceramic material, in the shape of a tube sealed at one end. The element body 1 has a pair of platinum electrodes 3 and 2 respectively on the exhaust gas side (the outer side) and the reference gas side (the inner side or air side).

The sensing element formed of the body 1 and the electrodes 2 and 3 is fitted in an exhaust manifold of an automobile engine through an electrically conductive holder 4 and a flange 5 so as to be set in the position where the sealed end of it can be exposed to exhaust gas flow.

The inner electrode 2 of the element is in electrical contact with a terminal 7 of a good electric conductor which is shaped like a pipe through a graphite ring 6. The air can come into the inner electrode 2 (reference which is on the gas side of the element) through the pipe of the terminal 7.

The outer electrode 3 is in electrical contact with the holder 4 of a good electric conductor through a graphite ring 8. In order to prevent leakage of the exhaust gas, a packing ring 9 in addition to the graphite ring 8 is set between the element and the holder 4.

By using the above oxygen sensor, an oxygen concentration can be sensed in the exhaust gas from the e.m.f. value which is generated between the electrodes 2 and 3 due to a difference between the oxygen concentrations of the exhaust gas and the air. The e.m.f. value E is expressed by the following equation:

$$E = (RT/4F) \log (P_1/P_2)$$

where $P_1$ and $P_2$ designate oxygen partial pressures of the air and the measured exhaust gas, respectively. T, R, and F denote an absolute temperature, gas constant, and Faraday's constant, respectively.

The outer electrode 3 is usually exposed to exhaust gas of high temperature and high pressure.

In general, in a usual oxygen sensor, a ceramic coating 10 having porous structure is formed as a cover on the surface of the outer electrode 3 by means of a plasma spray method in order to protect the electrode against damage of exhaust gas of high temperature and to slow down the rate of the gas flow toward the electrode. How much the gas flow rate should be slowed down depends on the particular engine. In forming the ceramic coating 10, it is important to make uniform the thickness thereof, because otherwise the degree of gas flow rate control varies from position to position on the ceramic coating.

The slowing down of the gas flow rate is necessary for lengthening the response time of the sensing element, which lengthening is necessary for making the sensing element response time match with the mechanical response time of the fuel supply mechanism in the engine. However, it is technically difficult to form a uniformly porous ceramic coating.

Further, conventionally, the sensor has two more protecting covers 11(a) and 11(b) with many holes, namely an outer cover 11(a) and an inner cover 11(b) as shown in FIG. 2, in order to protect the electrode 3 and the sensing body 1 from sudden thermal and mechanical shock of the exhaust gas flow, which are generated by combustion of fuel in the cylinders of the engine.

Recently, demand for sensors with a decreased number of protecting covers has arisen for the purpose of reducing the total price of the sensor. However, it is found that the sensing element in such a sensor, e.g., without an inner cover 11(b), is damaged by thermal shock because when the ceramic coating 10 is directly exposed to the exhaust gas flow, the ceramic coating (usually together with the sensing element) is likely to be broken. Further, when the ceramic coating 10 is removed, the sensing response time cannot be controlled.

SUMMARY OF THE INVENTION

Accordingly, it is an object of the invention to provide an oxygen gas sensor with a decreased number of covers, but without a deterioration of the performance of the oxygen gas sensor.

This object is achieved according to this invention by providing an oxygen sensor, for use in a high temperature gas flowing at a high speed, for sensing the oxygen concentration in the gas, the sensor comprising: an oxygen gas sensing element comprising a sensing body and an electrode; and a self supporting hollow cylindrical cap housing the sensing element in the hollow thereof in a manner that the sensing element is spaced from an inner wall of the cylindrical cap so that the electrode is exposed in the hollow, said cylindrical cap being formed of a sintered metal wool forming a metal wool web complex porous to the gas, with innumerable small meandering gas paths being formed in the metal wool web complex, whereby the cylindrical cap functions to weaken any mechanical shock and thermal shock to which the sensing element is exposed due to high flow pressure of the high temperature gas, and also functions to determine the sensing response time of the sensing element with a selected porosity of the metal wool web complex.

According to a further development of this invention, the metal wool is made of nickel-chromium alloy, a refractory stainless steel or nickel. Thereby, the protecting cap can be refractory and chemically stable in a high temperature gas atmosphere, particularly in automobile engine exhaust gases.

BRIEF DESCRIPTION OF THE DRAWINGS

Other objects and features of this invention will be apparent from the following detailed description taken together with the accompanying drawings, in which.

DETAILED DESCRIPTION OF THE PREFERRED EMBODIMENTS

An important characteristic of this invention is the use of a porous cap of a metal wool web complex in place of all the ceramic coating and the inner and the other protecting covers. The porous cap is made for example, by pressing and sintering metal wool of refractory metal. If a mechanical support for the porous cap is necessary, the outer cover can be revivedly used. Protection of the electrode and the ceramic sensing element body from exhaust gas of high temperature becomes possible by using the invention, because the porous cap of metal wool web complex has high thermal conductivity. Control of the flow rate of the exhaust gas toward the electrode becomes possible at the same time.

This invention will be more readily understood with reference to the following example, but it is intended to illustrate this invention only, and is not to be construed to limit thereby the scope of this invention.

EXAMPLE

Figure 3:
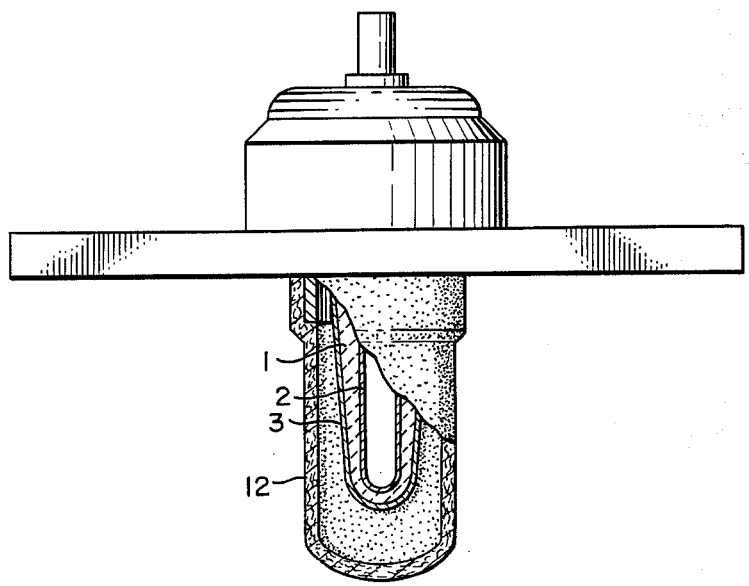
FIG. 3 is a front view, partially in cross section, of an example of an oxygen gas sensor according to this invention.

Referring to FIG. 3 an ionic conductive ceramic body 1 in the shape of a tube sealed at one end was prepared. The ceramic body 3 was made of a zirconia ceramic body containing 5 mol % yttria. Platinum electrodes 2 and 3 were respectively formed on the inner and outer surfaces of the ceramic body 1 by means of electroplating of platinum.

A porous cylindrical cap 12 was set on the element. This porous cap 12 was preliminarily prepared by pressing and sintering of metal wool such as a nickel-chromium alloy.

Figure 1:
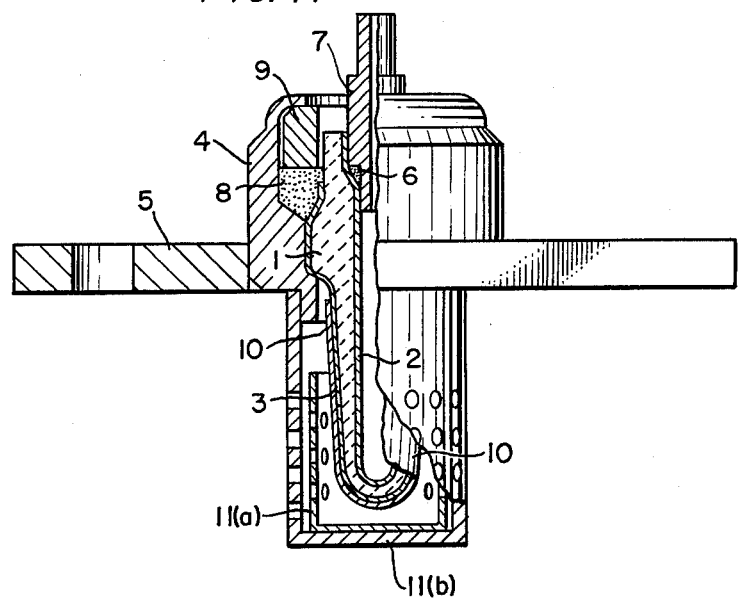
FIG. 1 is a front view, partially in cross section, of a conventional oxygen sensor.
Figure 2:
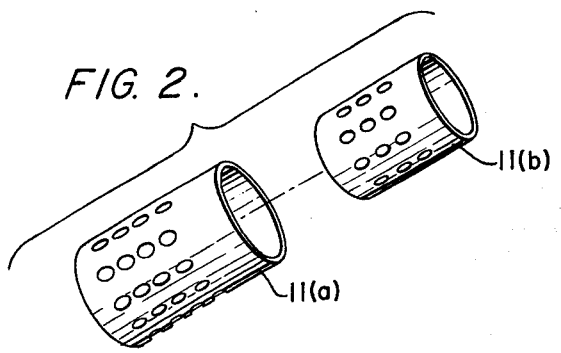
FIG. 2 is an exploded perspective view of protecting covers in FIG. 1.

By using the above prepared sensing element and using other members such as elements 4 to 9 in FIG. 1 in a per se well known manner, an oxygen sensor was constructed as shown in FIG. 3.

The gas flow rate through the porous cap 12 which was used in this example was in the range of 0.9 to 1.6 $l/cm^2 \cdot min$. In use of this sensor, the outer platinum electrode 3 is free from damage by exhaust gas of high temperature and high pressure, because the electrode 3 is not directly exposed to exhaust gas flow. When this oxygen sensor is subjected to a sudden thermal shock which occurs in the automobile engine, the porous cap 12 will weaken the shock, because the cap has high thermal conductivity, and the resultant heat is conveyed to the outer electrode and the ceramic body 1.

As shown in FIG. 3, a cylindrical space is found between the cap 12 and the sensing element. The space contributes to reducing any a damage to the sensing element by the above sudden thermal shock. The cap 12 acts as a protection cover of the outer electrode and the ceramic element body from impact of the sudden thermal shock.

The degree of slowing down of the gas flow rate through the cap can be easily controlled by choosing the porosity of the cap, more specifically by choosing the thickness (and hence the porosity) or sintering condition of the metal wool which is used to prepare the cap. For comparison, the sensors of two other types were prepared. One type (type A) was a conventional type with the sensing element covered with a ceramic coating and two protecting covers as shown in FIG. 1. The other type (type B) was with the element covered with a ceramic coating and one protecting cover, which is the same as the above FIG. 1 type except that here the inner cover 11(b) is removed. In both of these types, a zirconia ceramic element containing 5 mol % yttria with platinum electrodes prepared by means of electroplating was used.

Each of these three sensors was installed in a 2l automobile engine revolving at 5600 r.p.m. and subjected to an endurance test. In order to measure the degree of damage to the electrode by the exhaust gas flow, each testing sensor was removed from the engine equipment at 50 hour intervals, and measurements of internal electric resistance of the sensor between the inner electrode and the outer electrode through the ceramic body were carried out.

The measurement is described below. The sensor was set in a furnace at 400° C. which was filled with a combustible gas prepared by mixing based $N_2$ gas containing 0.8 volume percent $O_2$ gas and 4 volume percent $H_2$ gas. Then, the sensor becomes a concentration cell expressed as $$H_2-O_2, Pt/ZrO_2-Y_2O_3/Pt, air.$$

Then the measurement of the resistance of the sensor was carried out in these conditions.

Figure 4:
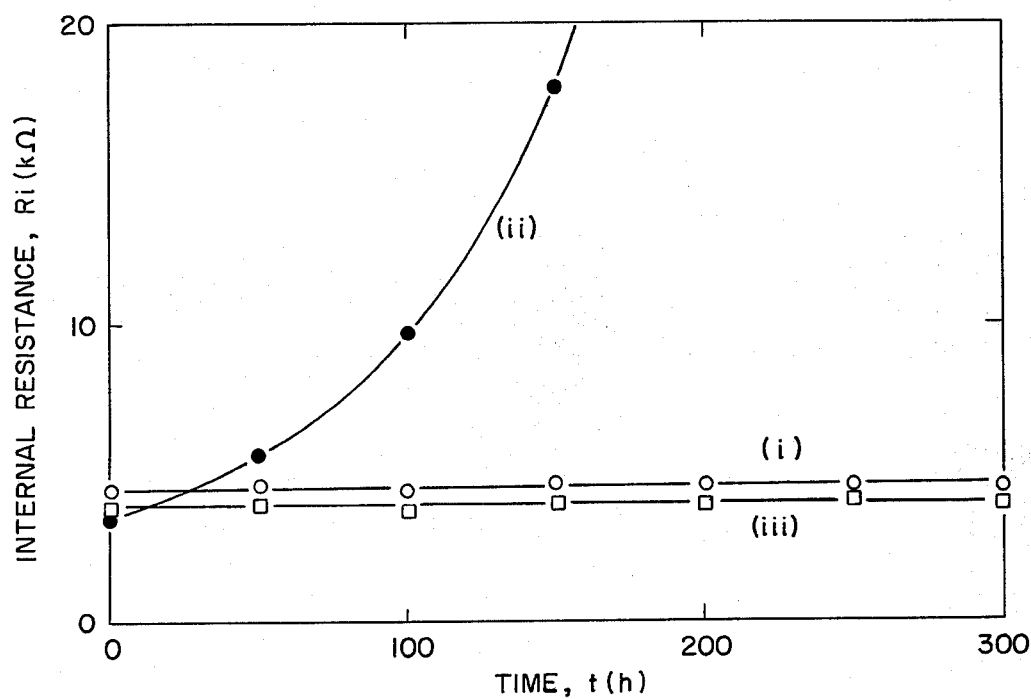
FIG. 4 is a graph showing dependence of the internal electric resistance of the sensor on the time of exposed to combustion gas in an endurance test.

The results of the measurement are shown in FIG. 4, wherein the curve (i) represents the results for the type A sensor, the curve (ii) represents the results for the type B sensor, and the curve (iii) represents the results for the sensor of the invention. As shown in FIG. 4, as reflected by the to endurance time, the value of the resistance of type B sensor increases. On the other hand, the values of the resistance for the type A sensor and this invention are substantially independent of the time of the endurance test.

An increase in the internal electric resistance indicates that the outer electrode is being partially damaged by the exhaust gas. It is found that the sensor of this invention is resistant to the damage by exhaust gas similar to that of the usual sensor with the two protecting covers and the ceramic coating.

This is attributed to the metal wool web complex, which substitutes for the conventional combination of the inner protecting cover and the ceramic coating, and which has innumerable small meandering gas paths. Thereby, the cylindrical cap functions to weaken the mechanical shock and thermal shock to the sensing element due to a high pressure flow of the high temperature gas, and also functions to determine the sensing response time of the sensing element. The porosity of the metal wool complex is controllable by controlling the conditions of pressing and/or sintering upon forming the metal wool complex.

After the 300 hour test, the type A sensor and the sensor of the invention were checked at the outer electrode surface. Thereby, it was found that in the case of the type A sensor, a substantial amount of carbon was deposited on the electrode under the ceramic coating. This indicates that the outer electrode, and thus the endurance of the sensor, will be deteriorated sooner. On the other hand, no carbon deposition was observed on the outer electrode in the case of the sensor in accordance with the invention. This is attributed to the feature that the sensing element is spaced from an inner wall of the cylindrical cap, whereby the electrode on the gas-flow side of the sensing element is exposed to the gas flow.

As modifications, nickel wool and a refractory stainless steel were respectively used in place of the nickel-chromium alloy wool. Thereby, it was found that similar excellent results were obtained with these different metal wools. These metals are good because they are refractory at high temperatures, and chemically stable in reducing atmospheres.

Figure 5:
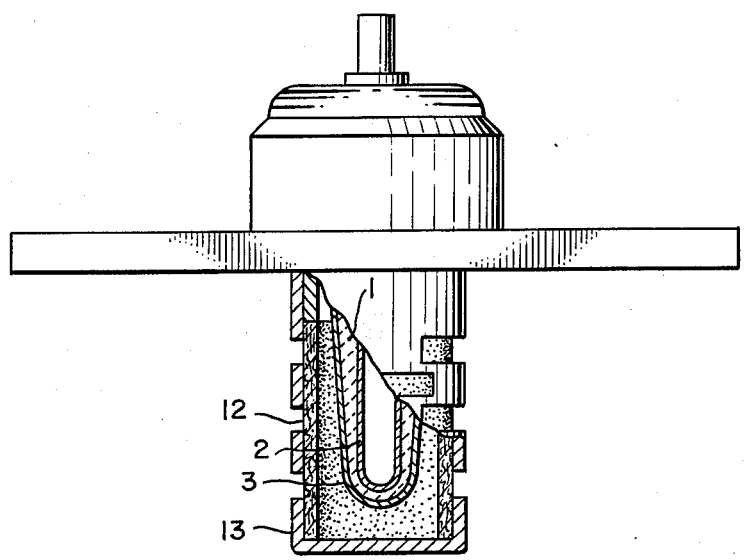
FIG. 5 is a front view, partially in cross section, of another example of an oxygen gas sensor according to this invention.
Figure 6:
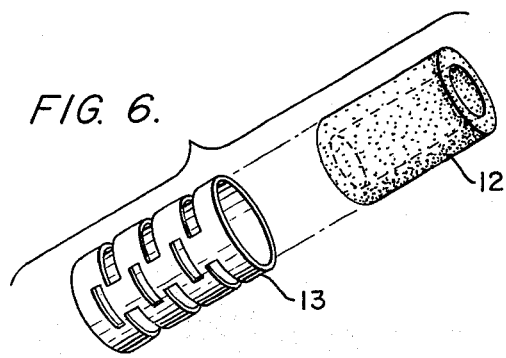
FIG. 6 is an exploded perspective view of the porous cap and the protecting cover in FIG. 5.

As a further modification, another type of sensor in accordance with this invention was made, as shown in FIGS. 5 and 6, which is the same as the type shown in FIG. 3, except that here a hollow cylindrical outer cover 13 is additionally provided. The cover 13 is made of a stainless steel having a lot of holes. It mechanically supports and houses the cap 12 in its hollow in such a manner that the outer wall of the cap 12 is in direct contact with the inner wall of the cover 13. It was found that the cover 13 increase the mechanical strength of the sensor without causing the the sensor performance to diminish.

What is claimed is:

1. An oxygen gas sensor for use in a high temperature gas flowing at a high speed and for sensing an oxygen concentration in the gas, said sensor comprising: an oxygen gas sensing element comprising a sensing body and an electrode; and a hollow cylindrical cap housing said sensing element in the hollow thereof in a manner that said sensing element is spaced from the inner surface of said cylindrical cap so as to expose said electrode in said hollow, said cylindrical cap being self supporting and being formed of a sintered metal wool forming a metal wool web complex porous to said gas, with innumerable small meandering gas paths being formed in said metal wool web complex, whereby said cylindrical cap functions to weaken mechanical shock and thermal shock to said sensing element due to the high flow pressure of the high temperature gas, and also functions to determine the sensing response time of said sensing element with a selected porosity of said metal wool web complex.

2. An oxygen gas sensor according to claim 1, wherein said metal wool is made of an nickel-chromium alloy.

3. An oxygen gas sensor according to claim 1, wherein said metal wool is made of a refractory stainless steel.

4. An oxygen gas sensor according to claim 1, wherein said metal wool is made of nickel.

5. An oxygen gas sensor according to claim 1, which further comprises a hollow cylindrical cover mechanically supporting and housing said cylindrical cap in the hollow thereof in a manner that the outer surface of said cylindrical cap is in direct contact with the inner surface of said cylindrical cover.

* * * * *